(12) United States Patent
Rothmann et al.

(10) Patent No.: US 8,852,863 B2
(45) Date of Patent: Oct. 7, 2014

(54) DETECTION OF MULTIPLE NUCLEIC ACID SEQUENCES IN A REACTION CARTRIDGE

(75) Inventors: Thomas Rothmann, Hilden (DE); Holger Engel, Hilden (DE); Ralf Himmelreich, Hilden (DE); Andy Wende, Hilden (DE); Rainer Dahlke, Hilden (DE)

(73) Assignee: Qiagen GmbH, Hilden (DE)

( * ) Notice: Subject to any disclaimer, the term of this patent is extended or adjusted under 35 U.S.C. 154(b) by 319 days.

(21) Appl. No.: 13/318,424

(22) PCT Filed: May 4, 2010

(86) PCT No.: PCT/EP2010/056030
§ 371 (c)(1),
(2), (4) Date: Jan. 18, 2012

(87) PCT Pub. No.: WO2010/128041
PCT Pub. Date: Nov. 11, 2010

(65) Prior Publication Data
US 2012/0107818 A1    May 3, 2012

(30) Foreign Application Priority Data
May 5, 2009  (EP) ..................................... 09159429

(51) Int. Cl.
*C12Q 1/68*    (2006.01)
*C12P 19/34*   (2006.01)

(52) U.S. Cl.
USPC ........................... 435/6.1; 435/6.12; 435/91.2

(58) Field of Classification Search
USPC ........................................ 435/6.1, 6.12, 91.2
See application file for complete search history.

(56) References Cited

U.S. PATENT DOCUMENTS

| | | | |
|---|---|---|---|
| 5,210,015 A * | 5/1993 | Gelfand et al. | 435/6.11 |
| 7,192,560 B2 * | 3/2007 | Parthasarathy et al. | 422/527 |
| 7,863,035 B2 * | 1/2011 | Clemens et al. | 435/287.1 |
| 7,981,604 B2 * | 7/2011 | Quake | 435/6.12 |
| 2004/0126770 A1 | 7/2004 | Kumar | |

FOREIGN PATENT DOCUMENTS

| | | |
|---|---|---|
| EP | 1935496 | 6/2008 |
| WO | WO 2004/074447 | 9/2004 |

* cited by examiner

*Primary Examiner* — Ardin Marschel
(74) *Attorney, Agent, or Firm* — Fanelli Haag & Kilger PLLC

(57) ABSTRACT

The present invention relates to a method for amplifying and detecting nucleic acid sequences in a reaction cartridge comprising, (i) providing a sample comprising at least one nucleic acid molecule, (ii) in a first reaction chamber of the cartridge providing reagents for an amplification reaction, (iii) mixing the sample with the amplification reagents, (iv) amplifying the at least one nucleic acid in the first reaction chamber of the cartridge, (v) transferring at least parts of the amplification reaction into a second and third reaction chamber of the cartridge each comprising a probe set and performing a melting point analysis in order to determine which of the probes has specifically bound a nucleic acid.

7 Claims, 9 Drawing Sheets

Fig. 8
A
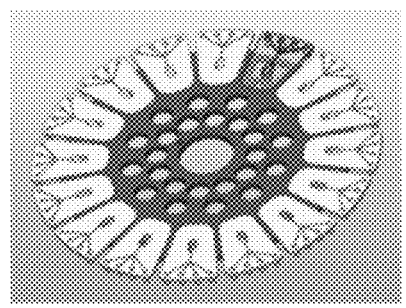
B
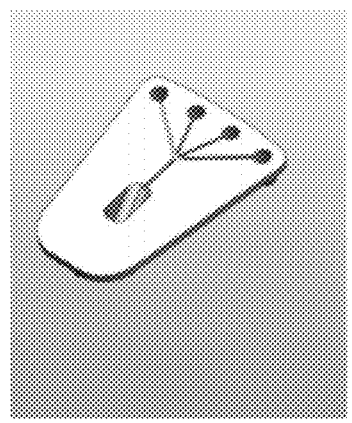
C
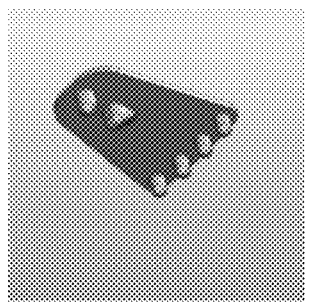

Fig. 9
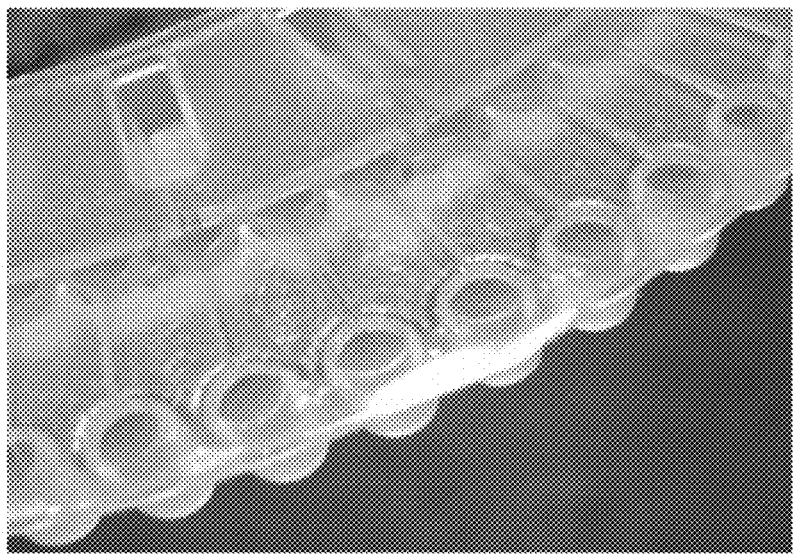
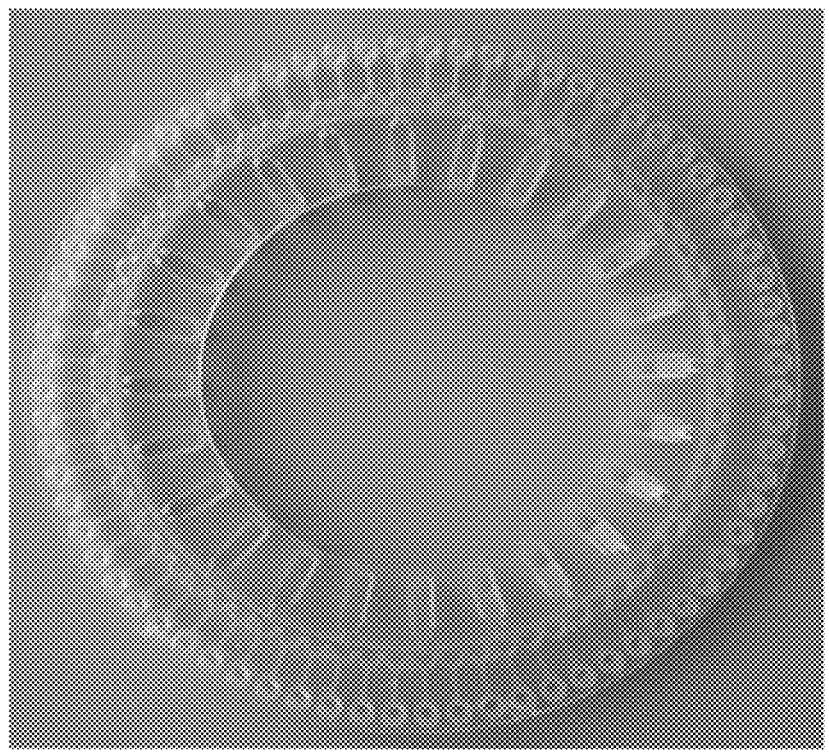

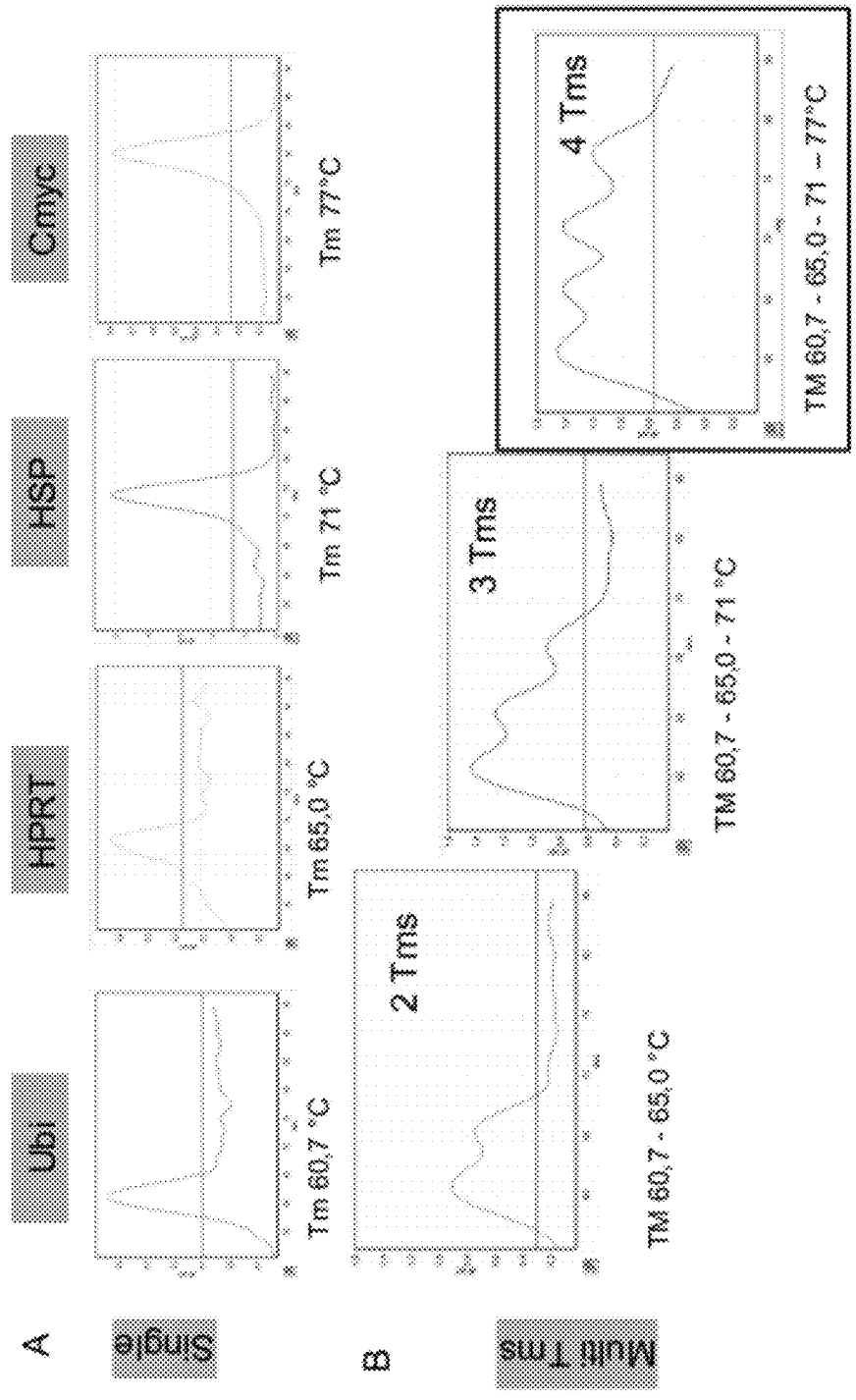

SEQUENCE LISTING

```
<160> NUMBER OF SEQ ID NOS: 24

<210> SEQ ID NO 1
<211> LENGTH: 17
<212> TYPE: DNA
<213> ORGANISM: Artificial
<220> FEATURE:
<223> OTHER INFORMATION: primer/probe

<400> SEQUENCE: 1
ttccacccat ggcaaat                                              17

<210> SEQ ID NO 2
<211> LENGTH: 20
<212> TYPE: DNA
<213> ORGANISM: Artificial
<220> FEATURE:
<223> OTHER INFORMATION: primer/probe

<400> SEQUENCE: 2
gaagatggtg atgggatttc                                           20

<210> SEQ ID NO 3
<211> LENGTH: 20
<212> TYPE: DNA
<213> ORGANISM: Artificial
<220> FEATURE:
<223> OTHER INFORMATION: primer/probe
```

```
<400> SEQUENCE: 3
caagcttccc gttctcagcc                                              20

<210> SEQ ID NO 4
<211> LENGTH: 21
<212> TYPE: DNA
<213> ORGANISM: Artificial
<220> FEATURE:
<223> OTHER INFORMATION: primer/probe

<400> SEQUENCE: 4
tcctcaaaag aaaccgtgca t                                            21

<210> SEQ ID NO 5
<211> LENGTH: 26
<212> TYPE: DNA
<213> ORGANISM: Artificial
<220> FEATURE:
<223> OTHER INFORMATION: primer/probe

<400> SEQUENCE: 5
agattaatgg ttgctaagga ctggat                                       26

<210> SEQ ID NO 6
<211> LENGTH: 29
<212> TYPE: DNA
<213> ORGANISM: Artificial
<220> FEATURE:
<223> OTHER INFORMATION: primer/probe

<400> SEQUENCE: 6
caccagcagt aactccccac aacctcttt                                    29

<210> SEQ ID NO 7
<211> LENGTH: 23
<212> TYPE: DNA
<213> ORGANISM: Artificial
<220> FEATURE:
<223> OTHER INFORMATION: primer/probe

<400> SEQUENCE: 7
tgccctgtgc agaagactat cta                                          23

<210> SEQ ID NO 8
<211> LENGTH: 20
<212> TYPE: DNA
<213> ORGANISM: Artificial
<220> FEATURE:
<223> OTHER INFORMATION: primer/probe

<400> SEQUENCE: 8
cgagctcaac aagtgcagtt                                              20

<210> SEQ ID NO 9
<211> LENGTH: 18
<212> TYPE: DNA
<213> ORGANISM: Artificial
<220> FEATURE:
<223> OTHER INFORMATION: primer/probe

<400> SEQUENCE: 9
aagtgacaga gtcaccaa                                                18

<210> SEQ ID NO 10
```

```
<211> LENGTH: 20
<212> TYPE: DNA
<213> ORGANISM: Artificial
<220> FEATURE:
<223> OTHER INFORMATION: primer/probe

<400> SEQUENCE: 10
tcaagaggtg ccacgtctcc                                              20

<210> SEQ ID NO 11
<211> LENGTH: 22
<212> TYPE: DNA
<213> ORGANISM: Artificial
<220> FEATURE:
<223> OTHER INFORMATION: primer/probe

<400> SEQUENCE: 11
tcttggcagc aggatagtcc tt                                           22

<210> SEQ ID NO 12
<211> LENGTH: 23
<212> TYPE: DNA
<213> ORGANISM: Artificial
<220> FEATURE:
<223> OTHER INFORMATION: primer/probe

<400> SEQUENCE: 12
cagcacaact acgcagcgcc tcc                                          23

<210> SEQ ID NO 13
<211> LENGTH: 25
<212> TYPE: DNA
<213> ORGANISM: Artificial
<220> FEATURE:
<223> OTHER INFORMATION: primer/probe

<400> SEQUENCE: 13
gttaagctgg ctgtcctgaa atatt                                        25

<210> SEQ ID NO 14
<211> LENGTH: 19
<212> TYPE: DNA
<213> ORGANISM: Artificial
<220> FEATURE:
<223> OTHER INFORMATION: primer/probe

<400> SEQUENCE: 14
ccccagcacc acattcatc                                               19

<210> SEQ ID NO 15
<211> LENGTH: 17
<212> TYPE: DNA
<213> ORGANISM: Artificial
<220> FEATURE:
<223> OTHER INFORMATION: primer/probe

<400> SEQUENCE: 15
tagtcgcctt cgtcgag                                                 17

<210> SEQ ID NO 16
<211> LENGTH: 22
<212> TYPE: DNA
<213> ORGANISM: Artificial
<220> FEATURE:
<223> OTHER INFORMATION: primer/probe

<400> SEQUENCE: 16
```

```
tggaacccac agtcattgat ga                                          22

<210> SEQ ID NO 17
<211> LENGTH: 22
<212> TYPE: DNA
<213> ORGANISM: Artificial
<220> FEATURE:
<223> OTHER INFORMATION: primer/probe

<400> SEQUENCE: 17
tgatctcctt gccaatggtg ta                                          22

<210> SEQ ID NO 18
<211> LENGTH: 27
<212> TYPE: DNA
<213> ORGANISM: Artificial
<220> FEATURE:
<223> OTHER INFORMATION: primer/probe

<400> SEQUENCE: 18
agatgctgcc ataactatg cccgagg                                      27

<210> SEQ ID NO 19
<211> LENGTH: 25
<212> TYPE: DNA
<213> ORGANISM: Artificial
<220> FEATURE:
<223> OTHER INFORMATION: primer/probe

<400> SEQUENCE: 19
ctcaacttta actggaaaga atgtc                                       25

<210> SEQ ID NO 20
<211> LENGTH: 19
<212> TYPE: DNA
<213> ORGANISM: Artificial
<220> FEATURE:
<223> OTHER INFORMATION: primer/probe

<400> SEQUENCE: 20 tcctttcac cagcaagct                                               19

<210> SEQ ID NO 21
<211> LENGTH: 26
<212> TYPE: DNA
<213> ORGANISM: Artificial
<220> FEATURE:
<223> OTHER INFORMATION: primer and probe

<400> SEQUENCE: 21
ttgctttcct tggtcaggca gtataa                                      26

<210> SEQ ID NO 22
<211> LENGTH: 20
<212> TYPE: DNA
<213> ORGANISM: Artificial
<220> FEATURE:
<223> OTHER INFORMATION: primer/probe

<400> SEQUENCE: 22
caagtctggg accaaagcgt                                             20

<210> SEQ ID NO 23
<211> LENGTH: 20
<212> TYPE: DNA
```

```
<213> ORGANISM: Artificial
<220> FEATURE:
<223> OTHER INFORMATION: probe/primer

<400> SEQUENCE: 23
aaaaccaaca ccgaactggc                                               20

<210> SEQ ID NO 24
<211> LENGTH: 27
<212> TYPE: DNA
<213> ORGANISM: Artificial
<220> FEATURE:
<223> OTHER INFORMATION: primer/probe

<400> SEQUENCE: 24
catggaagct ttgcaggctg gtgcaga                                       27
```

DETECTION OF MULTIPLE NUCLEIC ACID SEQUENCES IN A REACTION CARTRIDGE

This application is a National Stage of PCT/EP2010/056030, filed May 4, 2010 which claims priority to European Patent Application No. 09159429.1, filed 05/05/2009, the disclosure of which is incorporated herein by reference in its entirety.

FIELD OF THE INVENTION

The present invention is in the field of biology and chemistry, more in particular in the field of molecular biology and human genetics. The invention relates to the field of identifying certain nucleic acid sequences in a sample. Particularly, the invention is in the field of amplifying and detecting nucleic acid sequences in a reaction. The invention relates to a device and cartridge for detection of nucleic acid sequences in a sample.

The instant application contains a Sequence Listing which has been submitted in ASCII format via EFS-Web and is hereby incorporated by reference in its entirety. Said ASCII copy, created on Nov. 1, 2011, is named 0054_QI02_USI_sequencelisting.txt and is 4435 bytes in size.

BACKGROUND OF THE INVENTION

Diagnostic assays that sensitively, specifically, and quickly detect biological agents, e.g., pathogens, in samples are becoming increasingly important for both disease and diagnostic bio agent monitoring. Few assays are able to accurately detect physiologically or clinically relevant organisms on an appropriate time scale for the early detection of the presence of an infective or otherwise harmful agent.

A DNA microarray is a collection of microscopic DNA spots, commonly representing single genes, arrayed on a solid surface by covalent attachment to a chemical matrix. DNA arrays are different from other types of microarray only in that they either measure DNA or use DNA as part of its detection system. Qualitative or quantitative measurements with DNA microarrays utilize the selective nature of DNA-DNA or DNA-RNA hybridization under high-stringency conditions and fluorophore-based detection. DNA arrays are commonly used for expression profiling, i.e., monitoring expression levels of thousands of genes simultaneously, or for comparative genomic hybridization. The drawback with this system is that multiple steps need to be performed prior to analysis. Also, the array is not sensitive.

To date, the most sensitive detection methods involve PCR. Determining the presence or absence of a plurality of biological agents in a single sample can be performed using multiplexed detection methods.

Multiplex PCR uses multiple, unique primer sets within a single PCR reaction to produce amplicons of varying sizes specific to different DNA sequences, i.e. different transgenes. By targeting multiple genes at once, additional information may be gained from a single test run that otherwise would require several times the reagents and more time to perform. Annealing temperatures for each of the primer sets must be optimized to work correctly within a single reaction, and amplicon sizes, i.e., their base pair length, should be different enough to form distinct bands when visualized by gel electrophoresis.

Multiplexed real-time PCR is one method that can be used for a diagnostic assay. Assays based on PCR can be limited by the complexity of optimizing the PCR reactions to test for multiple agents in a cost-effective number of reaction tubes. As a general rule, the number of probes needed to support a highly specific confirmation result range from two to as many as six sequences. As one of skill in the art will be aware, optimizing a PCR reaction with many different primer pairs and probes can be a formidable task that becomes increasingly unmanageable as the number of targets to be detected increases. Assays based on PCR can also be limited by the number of unique labels available for analysis of results. For example, real-time PCR assays generally employ fluorescent labels.

The number of labels that can be used in a single reaction is limited by the number of fluorescent color channels available in the optical detection system used.

It would be advantageous to have a device and/or cartridge for simultaneously amplifying and detecting multiple nucleic acid sequences.

SUMMARY OF THE INVENTION

The present invention relates to a method for amplifying and detecting nucleic acid sequences in a reaction cartridge comprising the following steps, (i) providing a sample comprising at least one nucleic acid molecule, (ii) in a first reaction chamber of the cartridge providing reagents for an amplification reaction, (iii) mixing the sample with the amplification reagents, (iv) amplifying the at least one nucleic acid in the first reaction chamber of the cartridge, (v) transferring at least parts of the amplification reaction into a second and third reaction chamber of the cartridge each comprising a probe set, wherein (a) each probe set consists of at least three probes, (b) each of the probes is specific for a nucleic acid sequence, (c) there are at least two probes in each set which carry an identical label, (d) each of the probes in a given probe set that carries an identical label has a melting temperature ($T_m$) which differs by more than 5° C. from the other probe in said probe set with the same label, (e) wherein the probes carrying the identical label differ in melting temperature ($T_m$) in a way that they are distinguishable by melting point, (f) performing a melting point analysis in order to determine which of the probes has specifically bound a nucleic acid. One great advantage of the present invention is that the number of targets that may be analyzed is much bigger than in the prior art. Further the detection probes are separated which means they are not in the amplification reaction and hence, the polymerase does not digest them.

The invention also relates to a cartridge for performing a method for amplifying and detecting target nucleic acid sequences comprising, (i) a first reaction chamber for an amplification reaction, (ii) two or more further reaction chambers one of which comprises, at least three probes which are specific for a nucleic acid sequence, wherein at least two probes carry an identical label, wherein each of the probes that carry the same label have a melting temperature ($T_m$) which differs by more than 2° C. from the other probe with the same label, wherein the probes carrying the same label differ in melting temperature ($T_m$) in a way that they are distinguishable by melting point and a connection between said first and said two or more reaction chambers.

As used herein the term "cartridge" is, in the context of the present invention a device (preferentially microfluidic) which allows the transfer of the amplicon from the first reaction chamber to the second set of reaction chambers within a closed system. The cartridge may be made of polymer material. Preferred materials are polypropylen, polystyrol, COC, polycarbonat, PMMA etc. The material is preferably transparent with a low autoflouresence. The cartridge is preferably machined, hot embossed, or injection molded.

As used herein the term "nucleic acid sequence" is, in the context of the present invention, a sequence on a nucleic acid. A nucleic acid may be, inter alia, RNA, DNA, cDNA (complementary DNA), LNA (locked nucleic acid), mRNA (messenger RNA), mtRNA (mitochondrial), rRNA (ribosomal RNA), tRNA (transfer RNA), nRNA (nuclear RNA), siRNA (short interfering RNA), snRNA (small nuclear RNA), snoRNA (small nucleolar RNA), scaRNA (small Cajal Body specific RNA), microRNA, dsRNA (doubled-stranded RNA), ribozyme, riboswitch, viral RNA, dsDNA (double-stranded DNA), ssDNA (single-stranded DNA), plasmid DNA, cosmid DNA, chromosomal DNA, viral DNA, mtDNA (mitochondrial DNA), nDNA (nuclear DNA), snDNA (small nuclear DNA) or the like or any other class or sub-class of nucleic acid which is distinguishable from the bulk nucleic acid in a sample.

As used herein the term "probe" is a nucleic acid which is able to bind another nucleic acid.

As used herein the term "tissue" refers to any tissue or fluid in a human, animal or plant including, but not limited to breast, prostate, blood, serum, cerebrospinal fluid, liver, kidney, head and neck, pharynx, thyroid, pancreas, stomach, colon, colorectal, uterus, cervix, bone, bone marrow, testes, brain, neural tissue, ovary, skin, and lung.

As used herein the term "probe set" is a set of three or more agents that may interact with a nucleic acid molecule at a specific position, i.e. sequence.

Herein, a "label" is a moiety that is bound covalently or non-covalently to a probe where it can give rise to signal which may be detected by optical or other physical means.

DETAILED DESCRIPTION OF THE INVENTION

The present invention relates to a method for amplifying and detecting nucleic acid sequences in a reaction cartridge comprising the following steps, (i) providing a sample comprising at least one nucleic acid molecule, (ii) in a first reaction chamber of the cartridge providing reagents for an amplification reaction, (iii) mixing the sample with the amplification reagents, (iv) amplifying the at least one nucleic acid in the first reaction chamber of the cartridge, (v) transferring at least parts of the amplification reaction into a second and third reaction chamber of the cartridge each comprising a probe set, wherein (a) each probe set consists of at least three probes, (b) each of the probes is specific for a nucleic acid sequence, (c) there are at least two probes in each set which carry an identical label, (d) each of the probes in a given probe set that carries an identical label has a melting temperature ($T_m$) which differs by more than 2° C. from the other probe in said probe set with the same label, (e) wherein the probes carrying the identical label differ in melting temperature ($T_m$) in a way that they are distinguishable by melting point, (f) performing a melting point analysis in order to determine which of the probes has specifically bound a nucleic acid.

In an alternative embodiment each probe set consists of at least four probes and there are at least two probes in each set which carry an identical label.

In an alternative embodiment each probe set consists of at least five probes and there are at least two probes in each set which carry an identical label.

In an alternative embodiment each probe set consists of at least six probes and there are at least two probes in each set which carry an identical label.

In an alternative embodiment each probe set consists of at least six probes and there are at least two probes in each set which carry an identical label.

In an alternative embodiment each probe set consists of at least seven probes and there are at least two probes in each set which carry an identical label. Also three or more may have one label.

In an alternative embodiment each probe set consists of at least eight probes and there are at least two probes in each set which carry an identical label. Also three or more may have one label.

In an alternative embodiment each probe set consists of at least nine probes and there are at least two probes in each set which carry an identical label. Also three or more may have one label.

In an alternative embodiment each probe set consists of at least ten probes and there are at least two probes in each set which carry an identical label. Also three or more may have one label.

In one embodiment there are more than ten probes, at least three have an identical label and differ in melting temperature by at least 2° C.

The method is based on the basic principle that melting curve analysis is performed at the end of the amplification reaction with a single dual-labeled probe which allows differentiation of targets. The identically labeled probes differ in $T_m$. This analysis is done in the second and further chamber. Hydrolysis of these probes is avoided by its placement in the second and further chamber. This inventive concept for the first time allows the $T_m$ distribution to be made independent of the temperature at which the polymerase exhibits exo-activity. At the end of the PCR reaction or isothermal amplification process, the probes are allowed to hybridize and the mixture is subjected to stepwise increase in temperature, with fluorescence monitored continuously. As in classic TaqMan real-time PCR, generation of the fluorescence signal by the probe is based on the Förster resonance energy transfer (FRET) phenomenon. However, and contrary to what happens in TaqMan real-time PCR, no hydrolysis of the available probe molecules by Taq polymerase is involved in this embodiment. Rather, the procedure relies on the decrease in FRET observed when the probe detaches from its target to achieve a random single-stranded conformation.

The mean distance between the reporter and the quencher molecules of the dual-labeled probe will become shorter when the probe is released from its hybrid with the target sequence. Because the FRET effect is inversely proportional to the sixth power of this distance, a difference in fluorescence emission will be readily detectable between hybridized and melted configurations of the probe. A general scheme is shown in FIG. 6. Here, the change in fluorescence is shown cycle by cycle for different reaction temperatures. In a preferred embodiment of this method the polymerase used lacks a 5'-3' exonuclease activity.

The reaction volume of the amplification reaction is between 10 and 200 μl. Preferably, the reaction volume of the detection reaction is between 1 and 100μl.

The probes in the second and further chamber may be lyophilized, agarose or pectin or alginate embedded or simply dried down.

In order to better elucidate the invention we point to FIG. 1. A probe set according to the invention comprises at least two probes. In one embodiment a probe set may be seen as all those probes that share a common label but also as all those probes that share a common melting temperature ($T_m$). Ideally, the probes in a probe set that have the same label or labels that are not distinguishable from one another have different melting temperatures. The probes in a probe set that have identical or very similar melting temperatures should have different labels.

The person skilled in the art will know that the reagents will, ordinarily, comprise for example an enzyme for amplification, a buffer, nucleotides and the like. This of course depends on the type of amplification.

The inventors have developed a method which makes it possible to perform a multiplex amplification reaction with, for example, 20 templates. In one embodiment 5 different labels are used and all the probes that share a common label have a slightly varying melting temperature, ideally over 5° C. All the probes that share a common melting temperature on the other hand have a different label. By detecting the label and the melting temperature either during or after amplification the inventors have for the first time provided for a means which makes it possible to analyze, e.g. said 20 templates in one tube.

Probes with an identical label have a melting temperature that differs by more than 2° C., more than 3° C., more than 4° C., more than 5° C., more than 6° C., more than 7° C., more than 8° C., more than 9° C. or more than 10° C. The probes ideally differ by less than 18° C., less than 17° C., less than 16° C., less than 15° C., less than 14° C., less than 13° C., less than 12° C. or less than 11 ° C.

In principle this "detecting the amplified nucleic acids by determining whether the labeled probe has bound its nucleic acid sequence", and "detecting the temperature at which each given labeled probe dissociates from the nucleic acid sequence to which it has bound" may be done at the end of given reaction or during the reaction. Here, it is preferred that the detection is done after the amplification after amplifying the at least one nucleic acid in the first reaction chamber of the cartridge. The reaction is transferred at least in parts into a second and third reaction chamber of the cartridge each comprising a probe set, wherein each probe set consists of at least three probes, each of the probes is specific for a nucleic acid sequence, there are at least two probes in each set which carry an identical label, each of the probes in a given probe set that carries an identical label has a melting temperature ($T_m$) which differs by more than 5° C. from the other probe in said probe set with the same label, wherein the probes carrying the identical label differ in melting temperature ($T_m$) in a way that they are distinguishable by melting point, a melting point analysis is performed in order to determine which of the probes has specifically bound a nucleic acid.

Various amplification methods may be applied, these are for example, rolling circle amplification (such as in Liu, et al., "Rolling circle DNA synthesis: Small circular oligonucleotides as efficient templates for DNA polymerases," J. Am. Chem. Soc. 118:1587-1594 (1996).), isothermal amplification (such as in Walker, et al., "Strand displacement amplification--an isothermal, in vitro DNA amplification technique", Nucleic Acids Res. 20(7):1691-6 (1992)), ligase chain reaction (such as in Landegren, et al., "A Ligase-Mediated Gene Detection Technique," Science 241:1077-1080, 1988, or, in Wiedmann, et al., "Ligase Chain Reaction (LCR)—Overview and Applications," PCR Methods and Applications (Cold Spring Harbor Laboratory Press, Cold Spring Harbor Laboratory, N.Y., 1994) pp. S51-S64.). Polymerase chain reaction amplification is, however, preferred.

If the reaction is a polymerase chain reaction the "detecting the amplified nucleic acids by determining whether the labeled probe has bound its nucleic acid sequence", and "detecting the temperature at which each given labeled probe dissociates from the nucleic acid sequence to which it has bound" may be done after each cycle, after one cycle, after more than one cycle, in intervals, or at the end of the complete PCR reaction. In such a case part of the reaction is transferred after the respective cycle into the detection chambers.

A PCR reaction may consist of 10 to 100 "cycles" of denaturation and synthesis of a DNA molecule. In a preferred embodiment, the temperature at which denaturation is done in a thermocycling amplification reaction is between about 90° C. to greater than 95° C., more preferably between 92-94° C. Preferred thermocycling amplification methods include polymerase chain reactions involving from about 10 to about 100 cycles, more preferably from about 25 to about 50 cycles, and peak temperatures of from about 90° C. to greater than 95° C., more preferably 92-94° C. In a preferred embodiment, a PCR reaction is done using a DNA Polymerase I to produce, in exponential quantities relative to the number of reaction steps involved, at least one target nucleic acid sequence, given (a) that the ends of the target sequence are known in sufficient detail that oligonucleotide primers can be synthesized which will hybridize to them and (b) that a small amount of the target sequence is available to initiate the chain reaction. The product of the chain reaction will be a discrete nucleic acid duplex with termini corresponding to the ends of the specific primers employed. Any source of nucleic acid, in purified or non-purified form, can be utilized as the starting nucleic acid, if it contains or is thought to contain the target nucleic acid sequence desired. Thus, the process may employ, for example, DNA which may be single stranded or double stranded. In addition, a DNA-RNA hybrid which contains one strand of each may be utilized. A mixture of any of these nucleic acids may also be employed, or the nucleic acids produced from a previous amplification reaction using the same or different primers may be so utilized. The nucleic acid amplified is preferably DNA. The target nucleic acid sequence to be amplified may be only a fraction of a larger molecule or can be present initially as a discrete molecule, so that the target sequence constitutes the entire nucleic acid. It is not necessary that the target sequence to be amplified be present initially in a pure form; it may be a minor fraction of a complex mixture or a portion of nucleic acid sequence due to a particular animal which organism might constitute only a very minor fraction of a particular biological sample. The starting nucleic acid may contain more than one desired target nucleic acid sequence which may be the same or different. Therefore, the method is useful for amplifying simultaneously multiple target nucleic acid sequences located on the same or different nucleic acid molecules. The nucleic acid(s) may be obtained from any source and include plasmids and cloned DNA, DNA from any source, including bacteria, yeast, viruses, and higher organisms such as plants or animals. DNA may be extracted from, for example, blood or other fluid, or tissue material such as chorionic villi or amniotic cells by a variety of techniques such as that described by Maniatis et al., Molecular Cloning: A Laboratory Manual, (New York: Cold Spring Harbor Laboratory) pp 280-281 (1982). Additionally the Templex technology may be applied which combines Genaco's Tem-PCR technology and Luminex's xMAP technology.

The assay makes use of locus-specific primers. Oligonucleotide primers may be prepared using any suitable method, such as, for example, the phosphotriester and phosphodiester methods or automated embodiments thereof. In one such automated embodiment diethylophosphoramidites are used as starting materials and may be synthesized as described by Beaucage et al., Tetrahedron Letters, 22:1859-1862 (1981), which is hereby incorporated by reference. One method for synthesizing oligonucleotides on a modified solid support is described in U.S. Pat. No. 4,458,006, which is hereby incorporated by reference. It is also possible to use a primer which has been isolated from a biological source (such as a restriction endonuclease digest). Preferred primers have a length of from about 15-100, more preferably about 20-50, most preferably about 20-40 bases. It is essential that the primers of the method span the region comprising the target sequence. The target nucleic acid sequence is amplified by using the nucleic acid containing that sequence as a template. If the nucleic acid contains two strands, it is necessary to separate the strands of the nucleic acid before it can be used as the template, either as a separate step or simultaneously with the synthesis of the primer extension products. This strand separation can be accomplished by any suitable denaturing method including physical, chemical, or enzymatic means. One physical method of separating the strands of the nucleic acid involves heating the nucleic acid until it is completely (>99%) denatured. Typical heat denaturation may involve temperatures ranging from about 80° C. to 105° C., preferably about 90° C. to about 98° C., still more preferably 93° C. to 95° C., for times ranging from about 1 to 10 minutes. In the case of isothermal amplification the strand separation may also be induced by an enzyme from the class of enzymes known as helicases or the enzyme RecA, which has helicase activity and is known to denature DNA. The reaction conditions suitable for separating the strands of nucleic acids with helicases are described by Cold Spring Harbor Symposia on Quantitative Biology, Vol. XLIII "DNA: Replication and Recombination" (New York: Cold Spring Harbor Laboratory, 1978), and techniques for using RecA are reviewed in C. Radding, Ann. Rev. Genetics, 16:405-37 (1982), which is hereby incorporated by reference.

This synthesis can be performed using any suitable method. Generally, it occurs in a buffered aqueous solution. In some preferred embodiments, the buffer pH is about 7.5-8.9. Preferably, a molar excess (for cloned nucleic acid, usually about 1000:1 primer:template, and for genomic nucleic acid, usually about 106:1 primer:template) of the oligonucleotide primers is added to the buffer containing the separated template strands. It is understood, however, that the amount of complementary strand may not be known if the process herein is used for some applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

Nucleoside triphosphates, preferably dATP, dCTP, dGTP, dTTP and/or dUTP are also added to the synthesis mixture in adequate amounts. The preferred molarity of nucleotides is as follows 0.025 mM to 1 mM, preferred 0,05 to 0.6 mM, most prefered 0.1 to 0.5 mM.

It is preferred that the polymerase according to the invention is selected from the group of genera of *Thermus, Aquifex, Thermotoga, Thermocridis, Hydrogenobacter, Thermosynchecoccus* and *Thermoanaerobacter.*

It is preferred that the polymerase according to the invention is selected from the group of organisms of *Aquifex aeolicus, Aquifex pyogenes, Thermus thermophilus, Thermus aquaticus, Thermotoga neapolitana, Thermus pacificus, Thermus eggertssonii,* and *Thermotoga maritima.*

It is most preferred that the polymerase is Taq polymerase. However, as will be outlined in more detail below, in some embodiments it is preferred that the polymerase carries a 5'-3' exonuclease activity. In other embodiments it is preferred that the polymerase lacks a 5'-3' exonuclease activity. In most embodiments it is preferred that the polymerase lacks a 3'-5' exonuclease activity.

In one embodiment uracil residues are incorporated during the PCR reaction. Uracil DNA glycosylase (uracil-N-glycosylase) is the product of the *Escherichia coli* unggene, and has been cloned, sequenced and expressed in *E. coli.* Uracil DNA glycosylase (UDG) removes these uracil residues from DNA (single- and double-stranded) without destroying the DNA sugar-phosphodiester backbone, thus preventing its use as a hybridization target or as a template for DNA polymerases. The resulting abasic sites are susceptible to hydrolytic cleavage at elevated temperatures. Thus, removal of uracil bases is usually accompanied by fragmentation of the DNA. The person skilled in the art knows how to use the Uracil DNA glycosylase in order to avoid contamination. Likewise both the enzyme as well as the uracil nucleotide may be in the kit according to the invention.

Ideally, the labels of the probes in the first and second or further probe set are fluorescent labels and have an emission wavelength that is very similar. Ideally, that means they may be detected without altering the wavelength adjustment that may be detected by the detection device. It is preferred that the labels of the probes in the first, second and third or further probe set are identical.

It is preferred that the probes carrying the same label differ in melting temperature ($T_m$) in a way that they are distinguishable by melting point on a given instrument.

In one embodiment the melting transitions of the double stranded segments can be determined by monitoring fluorescence intensity of double stranded nucleic acid-specific (dsNAS) dyes. In one embodiment, the double stranded nucleic acid-specific dye is selected from the group consisting of SYBR® Green I, SYBR® Gold, ethidium bromide, propidium bromide, Pico Green, Hoechst 33258, YO-PRO-I and YO-YO-I, SYTO®9, LC Green®, LC Green® Plus+, EvaGreen™. These saturation dyes are capable of existing at sufficiently saturating conditions with respect to the DNA during or after amplification, while minimizing the inhibition of PCR. For example, at maximum PCR-compatible concentrations, the dsDNA binding dye has a percent saturation of at least 50%. In other embodiments, the percent saturation is at least 80%. In yet other embodiments, the percent saturation is at least 99%. It is understood that the percent saturation is the percent fluorescence compared to fluorescence of the same dye at saturating concentrations. Saturating concentration is the concentration that provides the highest fluorescence intensity possible in the presence of a predetermined amount of dsDNA. Because these dyes can be present at significantly higher concentrations without significantly interfering with certain nucleic acid reactions, these dyes may be particularly useful for monitoring the conformation of single-stranded nucleic acids and dsDNA.

The preferred reaction is a polymerase chain reaction.

It is preferred that the probes are selected from the group of TaqMan probe, molecular beacon probe, scorpion probe and light cycler probe. Detection of the amplification product per se may be accomplished by using one of the following probes, TaqMan probe, molecular beacon probe, scorpion probe, light cycler probe, hybridisation probe, displacement probe and other types of sequence specific probe formats.

The TaqMan® Assay utilizes the 5' nuclease activity of Taq DNA polymerase to cleave a fluorescently labeled probe (FAM™-labeled MGB).

Molecular beacons are single-stranded oligonucleotide hybridization probes that form a stem-and-loop structure (FIG. 2). The loop contains a probe sequence that is complementary to a target sequence, and the stem is formed by the annealing of complementary arm sequences that are located on either side of the probe sequence. A fluorophore is covalently linked to the end of one arm and a quencher is covalently linked to the end of the other arm. Molecular beacons do not fluoresce when they are free in solution. However, when they hybridize to a nucleic acid strand containing a target sequence they undergo a conformational change that enables them to fluoresce brightly. In the absence of targets, the probe is dark, because the stem places the fluorophore so close to the non-fluorescent quencher that they transiently share electrons, eliminating the ability of the fluorophore to fluoresce. When the probe encounters a target molecule, it forms a probe-target hybrid that is longer and more stable than the stem hybrid. The rigidity and length of the probe-target hybrid precludes the simultaneous existence of the stem hybrid. Consequently, the molecular beacon undergoes a spontaneous conformational reorganization that forces the stem hybrid to dissociate and the fluorophore and the quencher to move away from each other, restoring fluorescence. Molecular beacons are added to the assay mixture before carrying out gene amplification and fluorescence is measured in real-time. Molecular beacons can be synthesized that possess differently colored fluorophores, enabling the method according to the invention.

The color of the resulting fluorescence, if any, identifies the pathogenic agent in combination with the determination of the melting temperature.

Scorpion primers (FIG. 3) are bi-functional molecules in which a primer is covalently linked to the probe. The molecules also contain a fluorophore and a quencher. In the absence of the target, the quencher nearly absorbs the fluorescence emitted by the fluorophore. During the Scorpion PCR reaction, in the presence of the target, the fluorophore and the quencher separate which leads to an increase in the fluorescence emitted. The fluorescence can be detected and measured in the reaction tube.

A light cycler FRET probe system is a pair of single-stranded fluorescently-labeled oligonucleotides. Probe 1 (the donor probe) is labeled at its 3'-end with a donor fluorophore (generally fluorescein) and Probe 2 (the acceptor probe) is labeled at its 5'-end with one of four available fluorophores (red 610, 640, 670 or 705). The free 3' hydroxyl group of Probe 2 must be blocked with a phosphate group (P) to prevent Taq DNA polymerase extension. To avoid any steric problems between the donor and the acceptor fluorophores on both probes, there should be a spacer of 1 to 5 nt (4 to 25 Å distance) to separate the two probes from each other. Before any real-time quantitative PCR reaction takes place, fluorescence background may be observed inside the tube.

During the annealing step of real-time quantitative PCR, the PCR primers and the light cycler probes hybridize to their specific target regions causing the donor dye to come into close proximity to the acceptor dye. When the donor dye is excited by light from the light cycler instrument (hγ1), energy is transferred by Fluorescence Resonance Energy Transfer (FRET) from the donor to the acceptor dye. The energy transfer causes the acceptor dye to emit light (hγ2) at a longer wavelength than the light emitted from the instrument (hγ1). The acceptor fluorophore's emission wavelength is detected by the instrument's optical unit. The increase in measured fluorescent signal is directly proportional to the amount of accumulating target DNA.

Other alternative probes are Eclipse Probes (Epoch, Nanogen), displacement probes (Cheng et al., Nucleic Acids Research, 2004, Vol. 32, No. 7), pleiades probes (NAR 2007 Vol 35 5 e30) and plexor systems (Promega). Of course other probe systems are likewise encompassed by the invention.

In one embodiment of the invention the TaqMan probe is combined with a intercalating dye used for the melting point analysis.

In another embodiment the TaqMan probe is combined with a hybridization probe used for the melting point analysis, in a special embodiment the TaqMan probe is the hybridization probe. In another embodiment the TaqMan probe is not the hybridization probe but a separate oligonucleotide serves as hybridization probe.

Ideally, the cartridge comprises further reaction chambers for melting point analysis. Ideally, the cartridge comprises three or more reaction chambers for melting point analysis, four or more reaction chambers for melting point analysis, five or more reaction chambers for melting point analysis, six or more reaction chambers for melting point analysis, seven or more reaction chambers for melting point analysis or eight or more reaction chambers for melting point analysis.

Ideally, the cartridge is a throw-away article and the amplification and melting point analysis takes place when the cartridge is located in an amplification and detection device. Amplification may me achieved by different technologies as described before. The instrument processing the cartridge has to provide the adequate temperature profiles as defined by the amplification technology for the first reaction chamber. Irrespectively from the amplification technology the instrument has to provide the temperature profiles to perform a melting point analysis for the further reaction chambers.

In FIG. 4, the reaction comprises both a hybridization probe as well as a TaqMan probe. Here, (a) each probe set would, e.g. consists of at least two probes, wherein the probes are the hybridization probes, (b) each of the probes is specific for a nucleic acid sequence, (c) each of the hybridization probes (for example BHQ 1, BHQ 2, BHQ 3 in FIG. 4) in a given probe set carries a different label (see for example column A in FIG. 1), (d) all of the probes in a given probe set have a similar, preferably identical melting temperature ($T_m$) (see for example column A in FIG. 1) when they are dissociated from their target nucleic acid sequence by heating. The amplification of the nucleic acid sequences in the reaction is performed, the amplified nucleic acids are detected and the temperature at which each given labeled probe dissociates from the nucleic acid sequence to which it has bound is determined. In this embodiment it is preferred, although not essentially required, that the melting point of the hybridization probe is lower than the melting point of the primers used for amplification.

One example is given in FIG. 5. During the PCR reaction at a given melting point (the melting point for the hybridization probe Q1) the hybridization probe Q1 will dissociate for the DNA strand. The hybridization probe carries a quencher. Once dissociated, the downstream TaqMan probe will give rise to a signal coming from the fluorescent label which is now no longer quenched. The melting point is known due to the signal (melting point mp1). The label is known (FL1). Hence, it is possible to determine that this hybridization probe was specific for, e.g. pathogen 1 (p1) which is thus known to be present in the reaction. At the same time the TaqMan probe allows on line quantification during the PCR reaction. The detection step according to the invention would however take place in the second or further chamber.

It is an alternative that the reaction additionally comprises a double-strand nucleic acid specific dye. If a double-strand specific dye is used it is preferred that this dye is selected from the group of SYBR® Green I, SYBR® Gold, ethidium bromide, propidium bromide, Pico Green, Hoechst 33258, YO-PRO-I and YO-YO-I, SYBR® Green I is very preferred.

According to the invention ideally, the double-strand nucleic acid specific dye is spectrally distinguishable from the probe labels.

Ideally, the label is a fluorescent label and the label is selected from the group of FAM (5- or 6-carboxyfluorescein), VIC, NED, Fluorescein, FITC, IRD-700/800, CY3, CY5, CY3.5, CY5.5, HEX, TET, TAMRA, JOE, ROX, BODIPY TMR, Oregon Green, Rhodamine Green, Rhodamine Red, Texas Red, Yakima Yellow, Alexa Fluor PET, Biosearch Blue™, Marina Blue®, Bothell Blue®, Alexa Fluor®, 350 FAM™, SYBR® Green 1, Fluorescein, EvaGreen™, Alexa Fluor® 488 JOE™, VIC™, HEX™, TET™, CAL Fluor® Gold 540, Yakima Yellow®, ROX™, CAL Fluor® Red 610, Cy3.5™, Texas Red®, Alexa Fluor®, 568 Cy5™, Quasar™ 670, LightCycler Red640®, Alexa Fluor 633 Quasar™ 705, LightCycler Red705®, Alexa Fluor® 680, SYTO®9, LC Green®, LC Green® Plus+, EvaGreen™.

In a preferred embodiment, asymmetric primer concentrations are used. This is done by altering the ratio of both primers for each target in a way that the primer generating the DNA strand binding the probe is added at higher concentration than the other primer.

It is also preferred in this embodiment that the hybridization probes have a melting temperature ($T_m$) that is below the temperature at which the polymerase exhibits its optimal activity. This provides for that the hybridization probes dissociate and gives the way free for the polymerase to the TaqMan probe. It is obvious that the method ideally makes use of a polymerase that exhibits a 5'-3' exonuclease activity.

Real-time PCR requires an instrumentation platform that consists of a thermal cycler, a computer, optics for fluorescence excitation and emission collection, and data acquisition and analysis software. These machines, available from several manufacturers, differ in sample capacity (some are 96-well or 384-well standard plate format, others process fewer samples or require specialized glass capillary tubes, some have block format, others a carousel), method of excitation (some use lasers, others broad spectrum light sources with tunable filters or one or more diodes), detection (some use a camera, others a photo multiplier tube, or types of light detection system) and overall sensitivity. There are also platform-specific differences in how the software processes data. In principle the available machines harboring two or more detection channels are suited for the method according to the invention. In any case the device must hold the cartridge according to the invention (see also FIGS. 8 and 9).

Ideally the cartridge is a throw-away article and the amplification and melting point analysis takes place when the cartridge is located in a thermal cycler device or an amplification device restricted to isothermal amplifications.

In the method according to the invention, in one embodiment, the isothermal amplification device comprises a rotor and the amplification and melting point analysis takes place when the cartridge is in the rotor and the transfer of the at least parts of the amplification reaction into the second, third or further reaction chamber of the cartridge is done by means of centrifugation force.

The invention also relates to a cartridge for performing a method for amplifying and detecting target nucleic acid sequences comprising, (i) a first reaction chamber for an amplification reaction, (ii) two or more further reaction chambers one of which comprises, at least three probes which are specific for a nucleic acid sequence, wherein at least two probes carry an identical label, wherein each of the probes that carry the same label have a melting temperature ($T_m$) which differs by more than 2° C. from the other probe with the same label, wherein the probes carrying the same label differ in melting temperature ($T_m$) in a way that they are distinguishable by melting point and a connection between said first and said two or more reaction chambers.

Ideally the cartridge is a micro fluidic cartridge.

The cartridge may have a certain flow path (also termed "flow channel"), i.e. the route an applied fluid flows through said cartridge. The reaction chambers are arranged in the flow path, such that the fluid is passed through or to said modules. They may for example be arranged in series or in parallel, e.g. allowing for multiplexing. When arranged in series, the pore size of the porous barrier may decrease over the flow path to avoid clogging. The modules may comprise different or the same probes which may be fixed, in solution or dried. When comprising different probes, simultaneous detection of different analytes is possible. The probes may be present fixed on particles in the detection chambers.

The present invention thus combines properties of flow-through and flow-over devices so that the specific advantages of both types of devices are provided.

The reaction chambers may additionally comprise nucleic acids such as a DNA, RNA, aptamers, antibodies, Fab fragments, Fc tails. Additional probes may be proteins, such as e.g. receptors, antibodies. Additionally antibodies may be used in form of polyclonal or/and monoclonal antibodies.

It is preferred that the device holding the cartridge during the detection step further comprises a detection device ("detector"), preferably an optical read out. A detection device may be selected from the group consisting of a photodiode light sensor for measuring absorption or emission of light, CCD camera for measuring optical signals from an array of probes, confocal microscopy, GMR (giant magneto resistance) sensor—for magnetic particles, gamma detector (radio-isotopes), a capacitance bridge—for measuring changes in dielectric properties. Preferably, the detector may be a fluorescence detector for detecting fluorescence, e.g. of analytes comprising fluorescent labels. All optical detectors in this context may be termed "optical read out". In one embodiment for each detection chamber one detecting device is present in another embodiment two or more detection chambers share a common detector. The advantage with the rotor is that the chambers may fly by, i.e. pass the detector and only one is needed.

The cartridge is a device, preferentially microfluidic, that allows the fluid transfer from a first reaction vessel to at least two further reactions vessels within a closed system. The fluid transfer is achieved preferentially by centrifugal forces or pressure generating technologies (pumping mechanisms). The design of the fluidic connection between the reaction chambers enables the reaction fluid of the first chamber to be split in the required number of portions. This may be achieved by different means. For centrifugational fluid transfer the design of the connecting channels between the first and the second reaction chambers determines the centrifugal force needed to transfer the fluid. Alternatively valve technologies might be included in the cartridge design (not preferred) to regulate the fluid transfer between the chambers. The cartridge may be made of polymer material. Preferred materials are polypropylen, polystyrol, COC, polycarbonat, PMMA etc. The material is preferably transparent with a low autofluoresence. The cartridge is preferably machined, hot embossed, or injection molded.

The invention also relates to a cartridge according to the invention in a PCR device.

Primers and probes according to the invention may be specific for various targets, such as disease markers, pathogens, forensic markers or any other target that may be addressed by means of amplification. The invention is particularly suited for the analysis of pathogens. The most common bacterial disease is tuberculosis, caused by the bacterium Mycobacterium tuberculosis, which kills about 2 million people a year, mostly in sub-Saharan Africa. Pathogenic bacteria contribute to other globally important diseases, such as pneumonia, which can be caused by bacteria such as *Streptococcus* and *Pseudomonas*, and food borne illnesses, which can be caused by bacteria such as *Shigella, Campylobacter* and *Salmonella*. Pathogenic bacteria also cause infections such as tetanus, typhoid fever, diphtheria, syphilis and leprosy. One of the primary pathways by which food or water become contaminated is from the release of untreated sewage into a drinking water supply or onto cropland, with the result that people who eat or drink contaminated sources become infected. In developing countries most sewage is discharged into the environment or on cropland. This is the typical mode of transmission for the infectious agents of cholera, hepatitis A, polio and rotavirus. Thus, in one embodiment the primers and probes are specific for one or more pathogenic bacteria.

The cartridge may used for human or veterinary diagnosis, for testing food or water, for forensic applications or for scientific purposes.

EXAMPLE

Example 1

Embodiment of the Technical Concept of the Inventive Method for Multiplex Real-Time PCR Followed by Melting Curve Analysis with Fluorescently Labelled Probes In this experiment the feasibility of the technical concept shown in the figures shall be demonstrated. The reactions have been composed as shown in the tables below and were setup as quadruplicates and carried out with the protocol shown in table 6. For this purpose the reagents of table 8 were used. Composition of the 20× primer mixes and the 50× probe mix is indicated in table 2 and 3, respectively. Sequences of the primers and probes are shown in table 1. As template nucleic acid in PCR, PCR product was generated using cDNA from human leucocytes and the respective for and rev primers for each target shown in table 1, PCR product was purified using QiaQuick (Qiagen) PCR purification Kit and used at 1:1000 dilution. Templates were added to the individual reactions as given in table 9: In the first case "IC-only", only the Ubi template was added, functioning as internal positive control. In the second case, Ubi IC and target 1 Alb was added. In the third case, Ubi IC and target 2 Cmyc was used. In the fourth case, Ubi IC and Target 3 TBP was introduced. In the fifth case, Ubi IC and Target 4 GAP was added. For the sixth case, Ubi IC and target 5 SRY was added as template.

Real-time PCR was performed on a RotorGene 6000 PCR System (6-channel) with a 72 position rotor. Specification of the 6 detection channels are shown in table 5, including examples of fluorescent dyes suitable to be detected in the respective channels. Parameters for PCR cycling and subsequent melting curve are shown in table 6.

Subsequently the run data were analyzed with the appropriate instrument software. $C_T$ values observed in real-time PCR for the internal control (IC) and the respective targets are given in table 10. Melting points of the probes (maximum of melting peaks shown in FIG. 8) were determined and results are given in table 11. Observed melting peaks for the 6 different experimental conditions (table 9) for quadruplicate reactions are shown in FIG. 8. All reactions showed the expected result, showing CT values in the correct detection channel and melting peaks with the expected melting point for respective probe detecting the added target.

TABLE 1

Target Name and Primer/Probe Sequence

| Oligonucleotide Name | Sequence (5'-3') |
|---|---|
| GAPDH for (SEQ ID NO. 1) | TTCCACCCATGGCAAAT |
| GAPDH rev (SEQ ID NO. 2) | GAA GAT GGT GAT GGG ATT TC |
| PE-GAPDH-P (SEQ ID NO. 3) | CAA GCT TCC CGT TCT CAG CC |
| SRY-for (SEQ ID NO. 4) | TCC TCA AAA GAA ACC GTG CAT |
| SRY-rev (SEQ ID NO. 5) | AGA TTA ATG GTT GCT AAG GAC TGG AT |
| SRY-TM-FAM (SEQ ID NO. 6) | CAC CAG CAG TAA CTC CCC ACA ACC TCT TT |
| ALB for (SEQ ID NO. 7) | TGC CCT GTG CAG AAG ACT ATC TA |
| ALB rev (SEQ ID NO. 8) | CGA GCT CAA CAA GTG CAG TT |
| ALB Short(18 bp)_MK (SEQ ID NO. 9) | AAG TGA CAG AGT CAC CAA |
| PEc-myc-for (SEQ ID NO. 10) | TCA AGA GGT GCC ACG TCT CC |
| PEc-myc-rev (SEQ ID NO. 11) | TCT TGG CAG CAG GAT AGT CCT T |
| PEc-mycPro_MK (SEQ ID NO. 12) | CAG CAC AAC TAC GCA GCG CCT CC |
| UBI-TM.for (SEQ ID NO. 13) | GTT AAG CTG GCT GTC CTG AAA TAT T |
| UBI-TM.rev (SEQ ID NO. 14) | CCC CAG CAC CAC ATT CAT C |

TABLE 1 -continued

Target Name and Primer/Probe Sequence

| Oligonucleotide Name | Sequence (5'-3') |
|---|---|
| UBI Short(17 bp)_MK (SEQ ID NO. 15) | TAG TCG CCT TCG TCG AG |
| TBP_HE for (SEQ ID NO. 16) | TGG AAC CCA CAG TCA TTG ATG A |
| TBP_HE rev (SEQ ID NO. 17) | TGA TCT CCT TGC CAA TGG TGT A |
| TBP_MK (SEQ ID NO. 18) | AGATGCTGCCAATAACTATGCCCGAGG |

TABLE 2

Primer concentrations

| Target | Primer concentration 1x | Primer concentration 20x Primer Mix |
|---|---|---|
| GAPDH | FOR 0.4 µM REV 0.1 µM | FOR 8 µM REV 2 µM |
| SRY | FOR 0.1 µM REV 0.4 µM | FOR 2 µM REV 8 µM |
| ALB | FOR 0.1 µM REV 0.4 µM | FOR 2 µM REV 8 µM |
| cmyc | FOR 0.1 µM REV 0.4 µM | FOR 2 µM REV 8 µM |
| UBI | FOR 0.4 µM REV 0.1 µM | FOR 8 µM REV 2 µM |
| TBP | FOR 0.1 µM REV 0.4 µM | FOR 2 µM REV 8 µM |

TABLE 3

Probe concentrations

| Target | Probe concentration 1x | Probe Mix 50x |
|---|---|---|
| GAPDH (PE-GAPDH-P) | 0.3 µM | 15 µM |
| SRY (SRY-TM-FAM) | 0.3 µM | 15 µM |
| ALB (ALB Short(18 bp)_MK) | 0.8 µM | 40 µM |
| Cmyc (PEc-mycPro_MK) | 0.1 µM | 5 µM |
| UBI (UBI Short(17 bp)_MK) | 0.2 µM | 10 µM |
| TBP (TBP_MK) | 0.2 µM | 10 µM |

TABLE 4

Probe Labels (Oligonucleotide Name)

| Target | Probe Label 5'-3' |
|---|---|
| GAPDH (PE-GAPDH-P) | FAM-BHQ1 |
| SRY (SRY-TM-FAM) | FAM-BHQ1 |
| ALB (ALB Short(18 bp)_MK) | ROX-BHQ2 |
| Cmyc (PEc-mycPro_MK) | ROX-BHQ2 |
| UBI (UBI Short(17 bp)_MK) | LC670 BBQ |
| TBP (TBP_MK) | LC670 BBQ |

TABLE 5

Channel Specifications RotorGene 6000 instrument

| Channel | Excitation source/ Detection filter | Detected Dyes (Examples) |
|---|---|---|
| Blue | 365 ± 20 nm/460 ± 15 nm | Edans, Marina Blue ®, AMCA-X, Atto390, Alexa Fluor ® 350 |
| Green | 470 ± 10 nm/510 ± 5 nm | FAM ™, Fluorescein, Cyan 500 Alexa Fluor ® 488 |
| Yellow | 530 ± 5 nm/555 ± 5 nm | JOE ™, VIC ™, HEX ™, TET ™, Yakima Yellow ®, Cal Fluor Orange 560 |
| Orange | 585 ± 5 nm/610 ± 5 nm | ROX ™, Cy3.5 ®, Texas Red ®, Alexa Fluor ® 568, CAL Fluor ™ Red 610 |
| Red | 625 ± 10 nm/660 ± 10 nm | Cy5 ®, Quasar 670 ™, LightCycler Red 640 ®, Alexa Fluor ™ 633 |
| Crimson | 680 ± 5 nm/712 long pass | Quasar705 ™, LC Red 705 ®, LightCycler Red 670 Alexa Fluor ® 680 |

TABLE 6

PCR Cycling Parameters using QuantiFast Multiplex PCR Master Mix

| PCR | | |
|---|---|---|
| Initial PCR activation | 95° C. | 5 min |
| Denaturation | 95° C. | 30 s |
| Annealing/Extension | 60° C. | 30 s |
| Number of cycles | | 40x |
| Melting Curve | | |
| Pre Melt denaturation | 95° C. | 30 s |
| Melting programm | | |
| Ramp from | 55° C. | 95° C. |
| | 1 | Degree Celsius each step |
| Wait for | 90 s | Second of pre-melt conditioning on first step |
| Wait for | 5 s | Second for each step afterwards |

Software settings for melting curve: Gain optimization on each tube. The software routinely only collects melting data from one detection channel, therefore 3 subsequent melting curves were run, detecting melting data first from green, then from orange and then from crimson channel.

TABLE 7

Composition of multiplex PCR reaction mix

| Component | Final concentration |
|---|---|
| QuantiFast Multiplex PCR MM 2x | 1x |
| Primer mix 20x | 1x |
| Probe mix 50x | 1x |
| RNAse free water | Top up to 25 µl per reaction |
| Final reaction volume | 25 µl |

TABLE 8

Components and material numbers for TaqMelt 6plex PCR setup

| | |
|---|---|
| QuantiFast Multiplex PCR Master Mix | Both from: QuantiFast Multiplex PCR Kit, Qiagen, Material-# 204652 |
| RNAse free water | |
| GAPDH for | Supplier Tib MolBiol |
| GAPDH rev | http://www.tib-molbiol.de/de/ |
| PE-GAPDH-P | |
| SRY-for | |
| SRY-rev | |
| SRY-TM-FAM | |
| ALB for | |
| ALB rev | |
| ALB Short(18 bp)_MK | |
| PEc-myc-for | |
| PEc-myc-rev | |
| PEc-mycPro_MK | |
| UBI-TM for | |
| UBI-TM rev | |
| UBI Short(17 bp)_MK | |
| TBP_HE for | |
| TBP_HE rev | |
| TBP_MK | |

TABLE 9

Template PCR conditions

| Conditions | Expected Positive Signal (Detection Channel) | Expected Positive Signal (Detection Channel) |
|---|---|---|
| IC only | IC Ubi LC670 (Crimson) | — |
| IC + Target 1 | IC Ubi LC670 (Crimson) | Alb ROX (Orange) |
| IC + Target 2 | IC Ubi LC670 (Crimson) | Cmyc ROX (Orange) |
| IC + Target 3 | IC Ubi LC670 (Crimson) | TBP LC670 (Crimson) |
| IC + Target 4 | IC Ubi LC670 (Crimson) | GAP FAM (Green) |
| IC + Target 5 | IC Ubi LC670 (Crimson) | SRY FAM (Green) |

TABLE 10

$C_T$ Results Single Target + Internal Control (IC) Experiment

| | Channel | | |
|---|---|---|---|
| Name | Green | Orange | crimson |
| IC only | | | 21.0 |
| IC + Target 1 | | 22.2 | 21.1 |
| IC + Target 2 | | 17.1 | 21.1 |
| IC + Target 3 | | | 18.2 |
| IC + Target 4 | 16.0 | | 20.7 |
| IC + Target 5 | 16.4 | | 21.0 |

TABLE 11

Tm Results Single Target + Internal Control (IC) Experiment

| | Green | Orange | crimson | |
|---|---|---|---|---|
| Name | TM 1 | TM 1 | TM 1 | TM 2 |
| IC only | | | 63.5° C. | |
| IC + Target 1 | | 61.0° C. | 64.0° C. | |
| IC + Target 2 | | 73.8° C. | 64.0° C. | |
| IC + Target 3 | | | 64.3° C. | 70.3° C. |
| IC + Target 4 | 66.0° C. | | 64.0° C. | |
| IC + Target 5 | 72.2° C. | | 64.0° C. | |

Example 2

Realization of the Technical Concept of the Method for Multiplex Real-Time PCR Followed by Melting Curve Analysis for Different Probes Harbouring Distinguishable Tm's Detected in the FAM Detection Channel.

In this experiment the capability to distinguish several probes carrying the same label in the same detection channel is demonstrated. The reactions have been composed as shown in table 18 and were carried out with the protocol shown in table 17. For this purpose the reagents of table 18 & 19 were used. Composition of the 20× Primer Mixes and the 10pM Probe Mix is indicated in table 13 and 14, respectively. Sequences of the primers and probes are shown in table 12. As template, 10 ng /RxN cDNA generated from RNA from human leucocytes and the respective for and rev primers for each target shown in table 12. Singleplex reactions for each of the four target, duplex and triplex and quadruplex reactions were prepared and analysed. The seven different conditions and expected results are shown in table 20.

rtime PCR was performed on a RotorGene 6000 PCR System (6-channel) with a 72 position rotor. Specification of the 6 detection channels are shown in Table 16, including examples of fluorescent dyes suitable to be detected in the respective channels. Parameters for PCR cycling and subsequent melting curve are shown in Table 17.

Subsequently the run data were analyzed with the appropriate instrument software. Melting points of the probes (maximum of melting peaks shown in FIG. 9) were determined and results are given in Table 21.

TABLE 12

Target Name and Primer/Probe Sequence

| Oligonucleotide Name | Sequence (5'-3') |
|---|---|
| UBI-TM.5' (SEQ ID NO. 13) | GTT AAG CTG GCT GTC CTG AAA TAT T |
| UBI-TM.3' (SEQ ID NO. 14) | CCC CAG CAC CAC ATT CAT C |
| UBI Short_MK (SEQ ID NO. 15) | TAGTCGCCTTCGTCGAG |
| HPRT-TMfor (SEQ ID NO. 19) | CTCAACTTTAACTGGAAAGAATGTC |
| HPRT-TMrev (SEQ ID NO: 20) | TCCTTTTCACCAGCAAGCT |
| HPRT-TM (SEQ ID NO. 21) | TTGCTTTCCTTGGTCAGGCAGTATAATC |

TABLE 12 -continued

Target Name and Primer/Probe Sequence

| Oligonucleotide Name | Sequence (5'-3') |
|---|---|
| HSP89-TM.5' (SEQ ID NO. 22) | CAA GTC TGG GAC CAA AGC GT |
| HSP89-TM.3' (SEQ ID NO. 23) | AAA ACC AAC ACC GAA CTG GC |
| HSP (23 bp)_MK (SEQ ID NO. 24) | CAT GGA AGC TTT GCA GGC TGG TGC AGA |
| PEc-myc-for (SEQ ID NO. 10) | TCA AGA GGT GCC ACG TCT CC |
| Pec-myc-rev (SEQ ID NO. 11) | TCT TGG CAG CAG GAT AGT CCT T |
| HE_c-myc Penta Proben (HydrolEasy)_MK (SEQ ID NO: 12) | CAGCACAACTACGCAGCGCCTCC Modified with HYNA modifiers from Pentabse (www.pentabse.com) in order to increase the Tm to about 77° C. |

TABLE 13

Primer concentrations

| Target | Primer concentration 1x | Primer concentration 20x Primer Mix |
|---|---|---|
| UBI | FOR 0.1 µM REV 0.4 µM | FOR 8 µM REV 2 µM |
| HPRT | FOR 0.4 µM REV 0.1 µM | FOR 2 µM REV 8 µM |
| HSP | FOR 0.1 µM REV 0.4 µM | FOR 2 µM REV 8 µM |
| cmyc | FOR 0.1 µM REV 0.4 µM | FOR 2 µM REV 8 µM |

TABLE 14

Probe concentrations

| Target | Probe concentration 1x | Probe Mix 50x |
|---|---|---|
| UBI Short_MK | 0.2 µM | 10 µM |
| HPRT-TM | 0.2 µM | 10 µM |
| HSP (23 bp)_MK | 0.2 µM | 10 µM |
| HE_c-myc Penta Proben (HydrolEasy)_MK | 0.2 µM | 10 µM |

TABLE 15

Probe Labels (Oligonucleotide Name)

| Target | Probe Label 5'-3' |
|---|---|
| UBI Short_MK | FAM-BHQ1 |
| HPRT-TM | FAM-BHQ1 |
| HSP (23 bp)_MK | FAM-BHQ1 |
| HE_c-myc Penta Proben (HydrolEasy)_MK | FAM-BHQ1 |

TABLE 16

Channel Specifications RotorGene 6000 instrument

| Channel | Excittation source/ Detection filter | Detected Dyes (Examples) |
|---|---|---|
| Blue | 365 ± 20 nm/460 ± 15 nm | Edans, Marina Blue ®, AMCA-X, Atto390, Alexa Fluor ® 350 |
| Green | 470 ± 10 nm/510 ± 5 nm | FAM ™, Fluorescein, Cyan 500 Alexa Fluor ® 488 |
| Yellow | 530 ± 5 nm/555 ± 5 nm | JOE ™, VIC ™, HEX ™, TET ™, Yakima Yellow ®, Cal Fluor Orange 560 |
| Orange | 585 ± 5 nm/610 ± 5 nm | ROX ™, Cy3.5 ®, Texas Red ®, Alexa Fluor ® 568, CAL Fluor ™ Red 610 |
| Red | 625 ± 10 nm/660 ± 10 nm | Cy5 ®, Quasar 670 ™, LightCycler Red 640 ®, Alexa Fluor ™ 633 |
| Crimson | 680 ± 5 nm/712 long pass | Quasar705 ™, LC Red 705 ®, LightCycler Red 670 Alexa Fluor ® 680 |

TABLE 17

PCR Cycling Parameters using QuantiFast Multiplex PCR Master Mix

| PCR | | |
|---|---|---|
| Initial PCR activation | 95° C. | 5 min |
| Denaturation | 95° C. | 30 s |
| Annealing/Extension | 60° C. | 30 s |
| Number of cycles | | 40x |
| Melting Curve | | |
| Pre Melt denaturation | 95° C. | 30 s |
| Melting programm | | |
| Ramp from | 55° C. | 95° C. |
| | 1 | Degree Celsius each step |
| Wait for | 90 s | Second of pre-melt conditioning on first step |
| Wait for | 5 s | Second for each step afterwards |

Software Settings for melting curve: Gain optimization on each tube. Software only collect melting data from one detection channel

TABLE 18

Composition of multiplex PCR reaction mix

| Component | Final concentration |
|---|---|
| QuantiFast Multiplex PCR MM 2x | 1x |
| Primer Mix 20x | 1x |
| Probe 10 µM | 0.2 µM |

TABLE 18-continued

Composition of multiplex PCR reaction mix

| Component | Final concentration |
|---|---|
| RNAse free water | Top up to 20 µl per reaction |
| Final reaction volume | 20 µl |

TABLE 19

Components and material numbers for PCR setup

| | |
|---|---|
| QuantiFast Multiplex PCR Master Mix | Both from: QuantiFast Multiplex PCR Kit, Qiagen, Material-# 204652 |
| RNAse free water | |
| UBI-TM.5' | Supplier Tib MolBiol |
| UBI-TM.3' | http://www.tib-molbiol.de/de/ |
| UBI Short__MK | |
| HPRT-TMfor | |
| HPRT-TMrev | |
| HPRT-TM | |
| HSP89-TM.5' | |
| HSP89-TM.3' | |
| HSP (23 bp)__MK | |
| PEc-myc-for | |
| Pec-myc-rev | |
| HE__c-myc Penta Proben (HydrolEasy)__MK | Supplier Pentabase http://www.pentabase.com/ |

TABLE 20

Experiment PCR setup conditions

| Conditions | Expected Positive Signal (Detection Channel) |
|---|---|
| Single Ubi | 1 Tm |
| Single HPRT | 1 Tm |
| Single HSP | 1 Tm |
| Single cmyc | 1 Tm |
| Duplex Ubi, HPRT | 2 Tm's |
| Triplex HPRT, HSP, cmyc | 3 Tm's |
| 4plex Ubi, HPRT, HSP, cmyc | 4 Tm's |

TABLE 21

Tm Results Single Target + Internal Control (IC) Experiment

| Name | Green TM ° C. |
|---|---|
| Single Ubi | 60.7 |
| Single HPRT | 65.0 |
| Single HSP | 71.0 |
| Single cmyc | 77.0 |
| Duplex Ubi, HPRT | 60.7/65 |
| Triplex Ubi, HPRT, HSP | 60.7/65/71 |
| 4plex Ubi, HPRT, HSP, cmyc | 60.7/65.0/71/77° C. |

FIGURE CAPTIONS

FIG. 1

FIG. 1 shows the principle of the invention. The reactions performed with the probes in, e.g. row one all share a common label. However, the melting temperature of the probes differs. It is thus possible to identify each probe by means of the differing melting temperatures. The probes in column D for example all have the same melting temperature but a different label. It is thus possible to identify each probe by means of the different label.

FIG. 2

FIG. 2 shows the principle of a molecular beacon probe. Molecular beacons can be used as amplicon detector probes in for example diagnostic assays. Because non-hybridized molecular beacons are dark, it is not necessary to isolate the probe-target hybrids to determine the number of amplicons synthesized during an assay. They are thus ideally suited for the present invention. Molecular beacons are added to the assay mixture before carrying out gene amplification and fluorescence is measured in real-time.

FIG. 3

With Scorpion probes, sequence-specific priming and PCR product detection is achieved using a single oligonucleotide. The Scorpion probe maintains a stem-loop configuration in the unhybridized state. The fluorophore is attached to the 5'-end and is quenched by a moiety coupled to the 3'-end. The 3' portion of the stem also contains a sequence that is complementary to the extension product of the primer. This sequence is linked to the 5'-end of a specific primer via a non-amplifiable monomer. After extension of the Scorpion primer, the specific probe sequence is able to bind to its complement within the extended amplicon thus opening up the hairpin loop. This prevents the fluorescence from being quenched and a signal is observed.

FIG. 4

Figure shows one preferred embodiment of the invention. Here two probes are present in the reaction for each target sequence. A first hybridization probe is present that carries a label, e.g. a fluorescent label that is quenched by an adjacent TaqMan probe. When the melting temperature is reached the hybridization probe dissociates for the strand to which it is bound. The fluorescent label is now no longer quenched and a signal is produced.

FIG. 5

Figure shows one preferred embodiment of the invention. A fluorescent signal FL 1 at a melting temperature mp1 is indicative of the presence of the target sequence p1 in the reaction.

FIG. 6

FIG. 6 shows the intensity of a fluorescent signal with a single dual-labeled probe as it changes throughout a cycle as well as throughout the PCR. The signal is strong when it is bound to the target. It is weaker when dissociated. Also the signal gets stronger towards the end of the reaction due to the increase in template amount.

FIG. 7

FIG. 7 shows part of a cartridge for performing a method for amplifying and detecting target nucleic acid sequences comprising, (i) a first reaction chamber for an amplification reaction, (ii) two or more further reaction chambers one of which comprises, at least three probes which are specific for a nucleic acid sequence, wherein at least two probes carry an identical label, wherein each of the probes that carry the same label have a melting temperature ($T_m$) which differs by more than 5° C. from the other probe with the same label, wherein the probes carrying the same label differ in melting temperature ($T_m$) in a way that they are distinguishable by melting point, (iii) a connection between said first and said two or more reaction chambers.

FIG. 8

FIG. 8A shows the rotor with numerous cartridges according to the invention placed on/in the rotor. Each cartridge has a first chamber for the amplification reaction and three further chambers for the detection. The rotor speed is used to spin the PCR reaction into the detection chambers. The cartridges have microfluidic channels. The cartridges may be snap hooked into the rotor. The rotor may be run in a Corbett Real Time Cycler. 24 PCR reaction chambers are shown with 72 detection chambers. Given that each chamber detects, e.g. 24 probes, the rotor can analyze 1728 targets in one reaction.

FIG. 8B shows a single cartridge top view.

FIG. 8C shows a single cartridge bottom view.

FIG. 9

FIG. 9 shows various cartridge embodiments. Here multiple cartridges are made in one plastic piece.

FIG. 10

Figure 1:
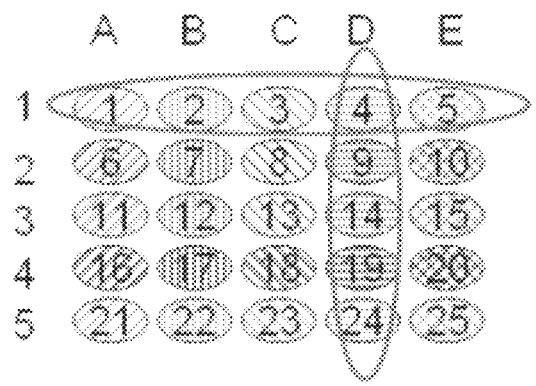
Figure 2:
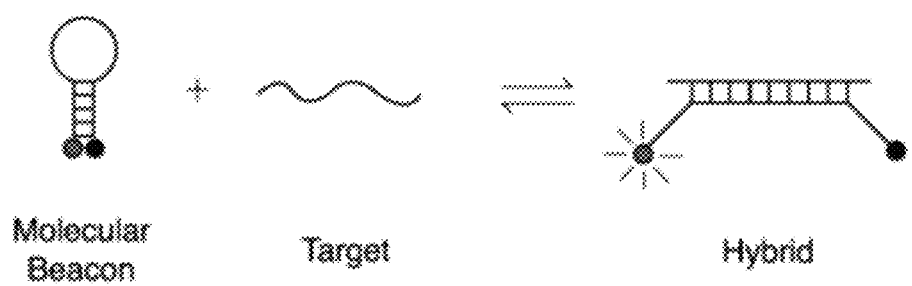
Figure 3:
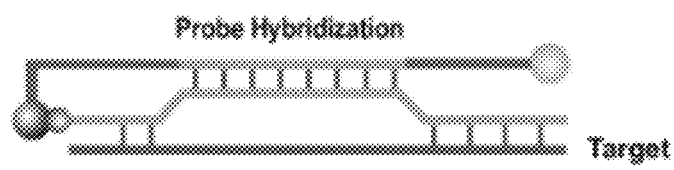
Figure 4:
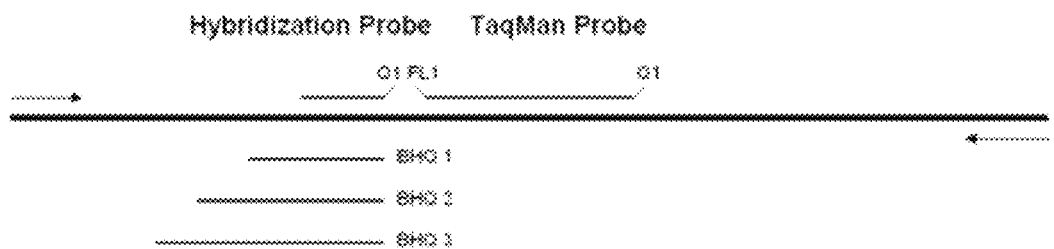
Figure 5:
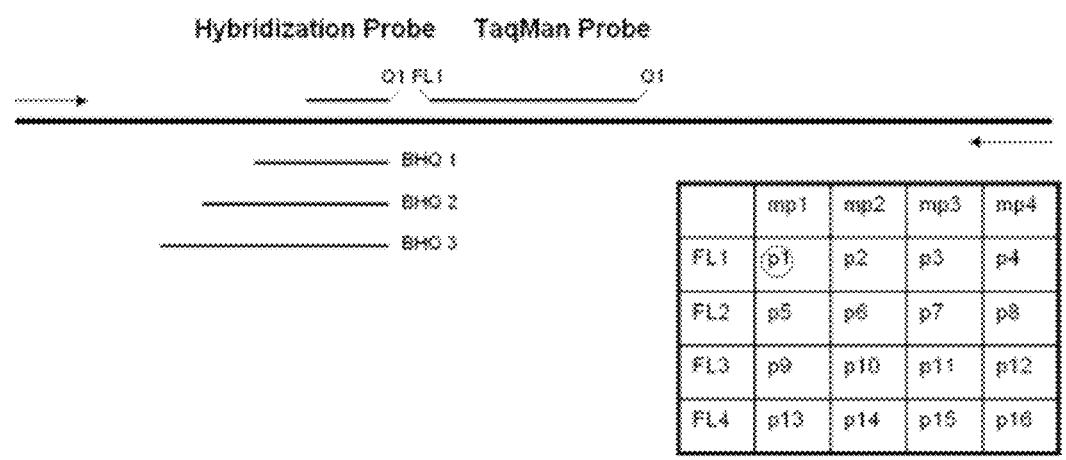
Figure 6:
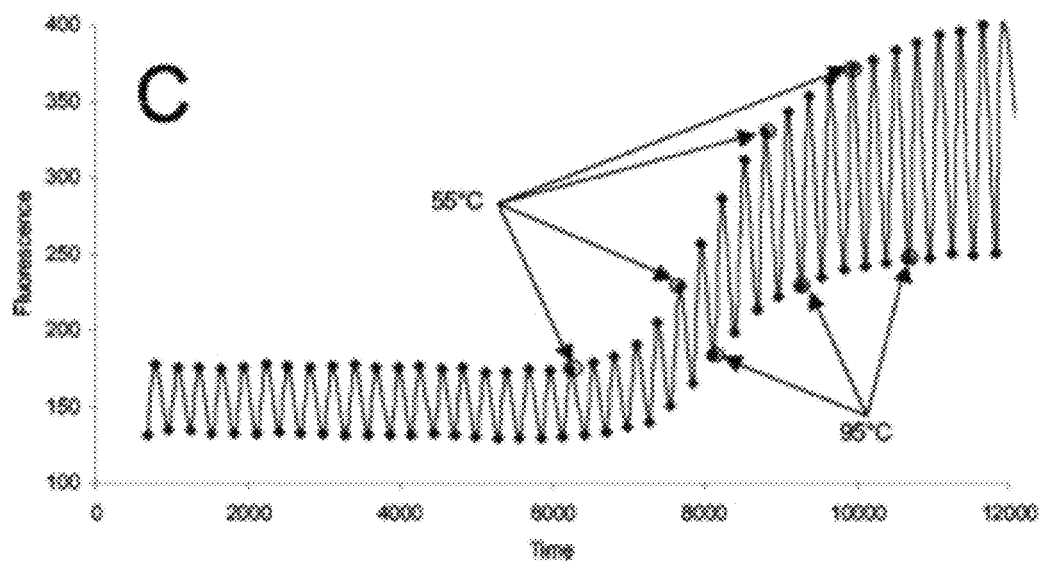
Figure 7:
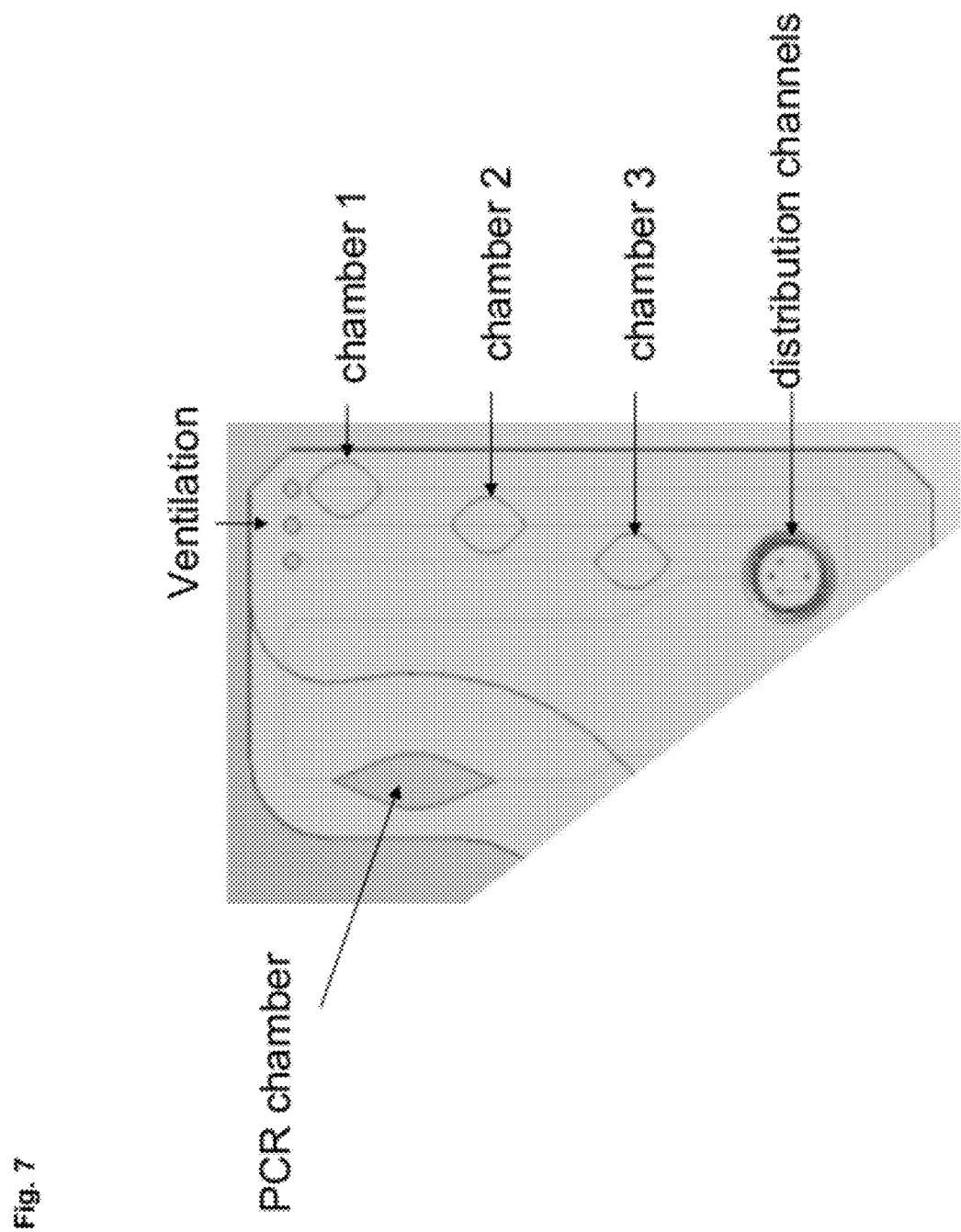
Figure 10:
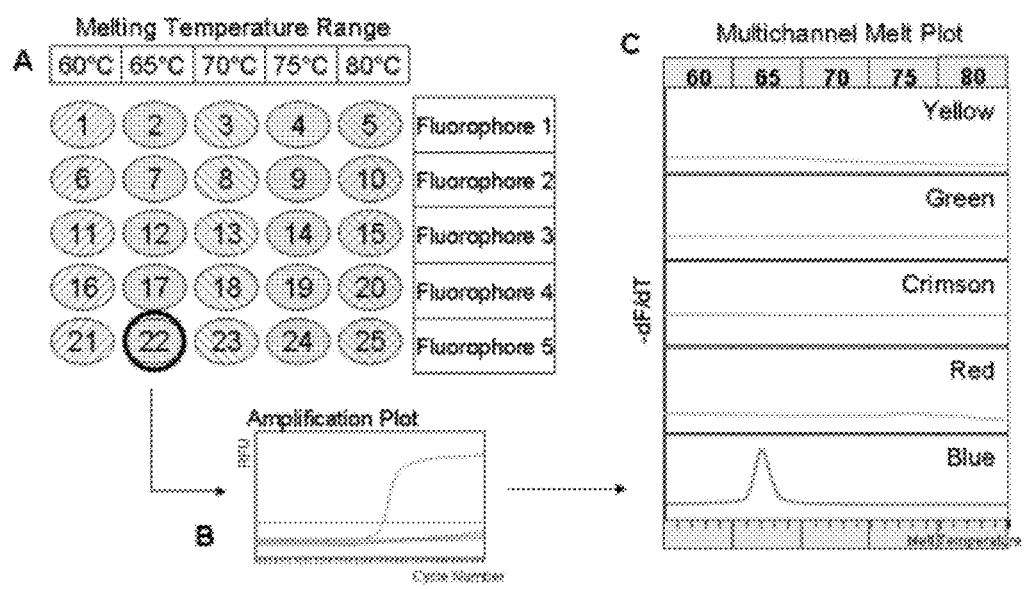

FIG. 10 shows the workflow of the invention. In panel A, a preferred embodiment of the invention already described above, is shown. The reactions performed with the probes in, e.g. row one all share a common label. However, the melting temperature of the probes differs by about 5° C., ranging from about 60° C. to about 80° C., as indicated above panel A. The given probe melting temperatures range from about 60° C. (about means about +/−10% deviation) to about 80° C. is preferred when the probe signal is also detected in real-time PCR, since these temperature are well compatible to typical PCR parameters. In the example, target 22 is contained in the sample. In panel B, the result for real-time PCR for such a multiplex assay is schematically shown for a case where target 22 (indicated by the black circle) is contained in the sample, noticeable by an increasing amplification plot in the detection channel detecting the label contained on the probe for target 22. Acquiring the real-time PCR data is an optional step, but not essential for performing the methodology of the invention. In FIG. 1C, the results of a multichannel melting curve experiment performed at a stage of the reaction where sufficient product is present to generate a signal. In a preferred embodiment, this is done in the plateau phase of the reaction. By performing a multichannel melting curve analysis, it is thus possible to identify each probe by means of the differing melting temperatures. The probes in column D for example all have the same melting temperature but a different label. It is thus possible to identify each probe by means of the different label, which makes the multichannel melting curve analysis the central element of the invention. The shown melting peaks represent the dF/dT signal, where the maximum of the peaks is referred to as the melting point of the respective probe.

FIG. 11

Figure 11:
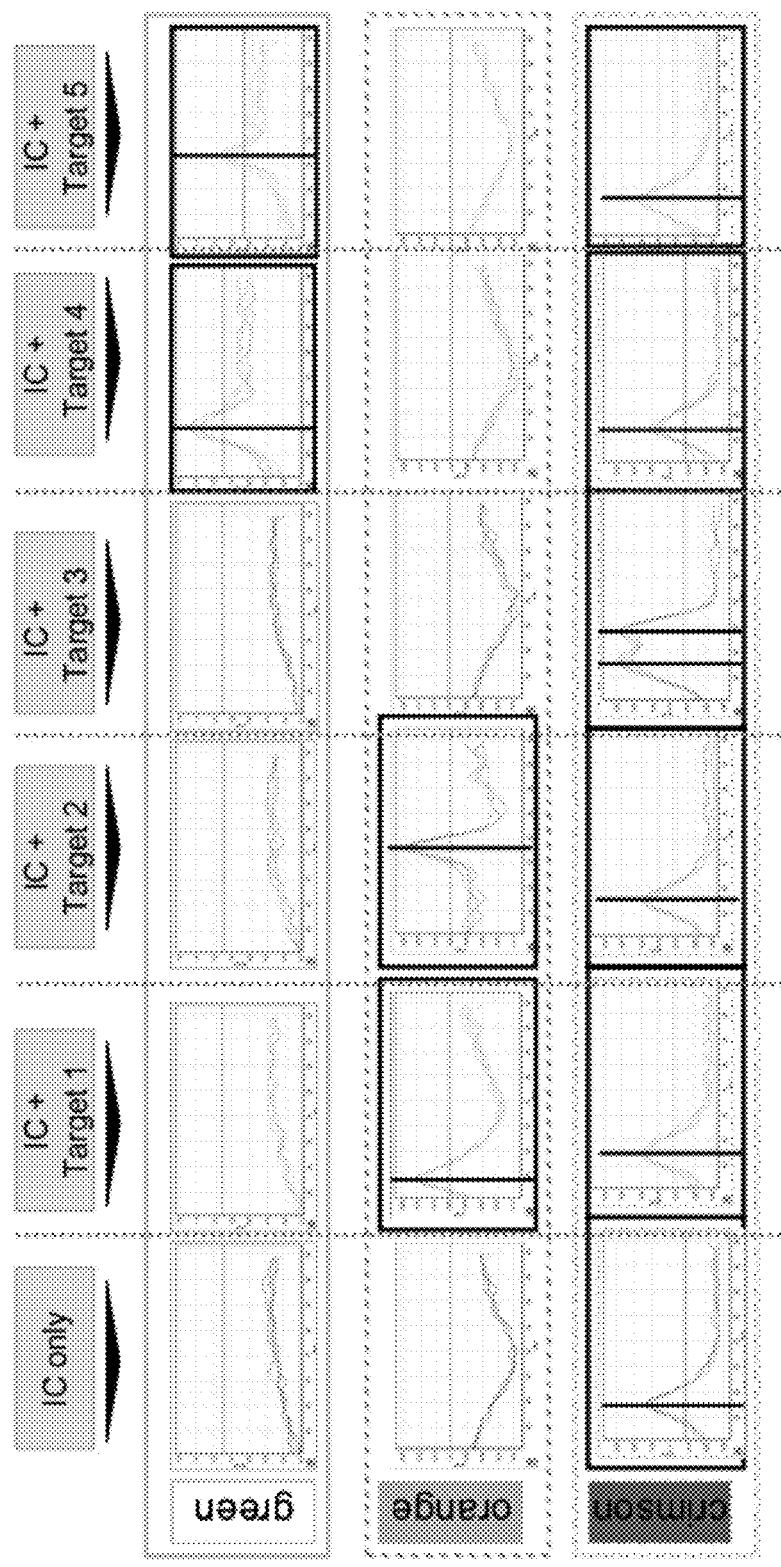

FIG. 11 shows the results of the multichannel melting curve analysis from the example. Fluorescent melting curves of quadruplicate reactions obtained for the template PCR conditions from the table. Horizontal panels marked with "green", "orange" and "crimson" indicate the signals obtained in the respective detection channels specified in the tables. The sets of data separated by the dotted horizontal line represent the results for the six different template PCR conditions from table 9, clearly showing only the expected positive melting peak signal in the expected detection channel and the expected melting point, with the positive control (internal control) always being reliably positive. Obtained melting points are summarized in table 11.

FIG. 12

FIG. 12 shows the results of the Post-PCR melting curve analysis from example 2. In panel A, fluorescent melting peaks (df/dT) of singleplex reactions for reactions obtained for the experiment PCR conditions from Table 20 are shown. The measured melting point for each of the four probes is shown below the respective picture and is summarized in table 21.

In panel B, fluorescent melting peaks (df/dT) (from left to right) first of a duplex for Ubi and HPRT, second for a triplex for Ubi, HPRT and HSP, and fourth (with black frame) a quadruplex for Ubi, HPRT, HSP and Cmyc is shown. The measured melting point for each of the four probes is shown below the respective picture and is summarized in table 21. Obtained melting points are summarized in Table 21. These data clearly demonstrate that the several probes carrying the same label can be clearly distinguished by their melting point.

The invention claimed is:

1. Method for amplifying and detecting nucleic acid sequences in a reaction cartridge comprising the following steps:
   (i) providing a sample comprising at least one nucleic acid molecule and a throw-away microfluidic cartridge,
   (ii) in a first reaction chamber of the cartridge providing reagents for an amplification reaction,
   (iii) mixing the sample with the amplification reagents,
   (iv) amplifying the at least one nucleic acid in the first reaction chamber of the cartridge,
   (v) transferring at least parts of the amplification reaction into a second and third reaction chamber of the cartridge each comprising a probe set, wherein
      a) each probe set consists of at least three probes,
      b) each of the probes is specific for a nucleic acid sequence;
      c) there are at least two probes in each set which carry an identical label, wherein the label is a fluorescent label,
      d) each of the probes in a given probe set that carries an identical label has a melting temperature ($T_m$) which differs by more than 2° C. from the other probe in said probe set with the same label,
      e) wherein the probes carrying the identical label differ in melting temperature ($T_m$) in a way that they are distinguishable by melting point,
   (vi) performing a melting point analysis in the second and/or third reaction chamber in order to determine which of the probes has specifically bound a nucleic acid,
      wherein the amplification and melting point analysis takes place when the cartridge is located in an amplification device, and
      wherein the cartridge comprises a connection between the first reaction chamber and the second and/or third reaction chamber.

2. The method of claim 1, wherein the amplification reaction is a multiplex polymerase chain reaction.

3. The method of claim 1, wherein at least one of the probe sets comprises at least three probes with identical label.

4. The method of claim 1, wherein the cartridge comprises further reaction chambers for melting point analysis.

5. The method of claim 1, wherein the amplification device comprises a rotor and the amplification and melting point analysis takes place when the cartridge is in the rotor and the transfer of the at least parts of the amplification reaction into the second, third or further reaction chamber of the cartridge is done by centrifugation force.

6. The method of claim 1, wherein the probes are selected from the group consisting of TaqMan probe, molecular beacon probe, scorpion probe, light cycler probe, hybridisation probe and displacement probe.

7. The method of claim 1, wherein the label is a fluorescent label and the label is selected from the group consisting of blue fluorescent dyes (Marina Blue®, Bothell Blue®, Alexa fluor® 350, Biosearch Blue™), green fluorescent dyes (FAM™, SYTO®g, LC Green®, LC Green®Plus+, EvaGreen™, SYBR® Green 1, Alexa fluor®488, yellow fluorescent dyes (JOE™, VIC™, HEX™, TET™, Yakima Yellow™), orange fluorescent dyes (ROX, Cy3.5, Texas Red, Alexa Fluor 568, CAL Fluor Red 610), red fluorescent dyes (Cy5, Quasar®670, LightCycier Red 640, Alexa Fluor®633), crimson fluorescent dyes (Quasar®70S, Alexa Fluor®680) and yellow-green fluorescent dyes (CAL Fluor Gold 540).

* * * * *